(12) United States Patent
Sekine et al.

(10) Patent No.: US 7,943,758 B2
(45) Date of Patent: May 17, 2011

(54) 3'-END NUCLEOSIDE UNIT COMPRISING PHOSPHORAMIDITE

(75) Inventors: Mitsuo Sekine, Yokohama (JP); Kohji Seio, Yokohama (JP); Akihiro Ohkubo, Machida (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 963 days.

(21) Appl. No.: 10/590,268

(22) PCT Filed: Feb. 10, 2005

(86) PCT No.: PCT/JP2005/002058
§ 371 (c)(1),
(2), (4) Date: Jan. 8, 2007

(87) PCT Pub. No.: WO2005/080411
PCT Pub. Date: Sep. 1, 2005

(65) Prior Publication Data
US 2008/0039620 A1    Feb. 14, 2008

(30) Foreign Application Priority Data
Feb. 25, 2004   (JP) ................... 2004-049312

(51) Int. Cl.
*C07H 19/10*   (2006.01)
*C07H 19/20*   (2006.01)

(52) U.S. Cl. .................. 536/26.7; 536/26.8

(58) Field of Classification Search .......... None
See application file for complete search history.

(56) References Cited

FOREIGN PATENT DOCUMENTS
JP    7-112997 A    5/1995
WO    WO-02/20543 A2    3/2002

OTHER PUBLICATIONS

Takeshi Wada et al.; Functionalization of Solid Supports with N-Unprotected Deoxyribonucleosides; Tetrahedron Letters; 39, 1998, pp. 5593-5596.

*Primary Examiner* — Lawrence E Crane
(74) *Attorney, Agent, or Firm* — Birch, Stewart, Kolasch & Birch, LLP

(57) ABSTRACT

Methods of synthesizing nucleic acid oligomers on a solid-phase support having a 3'-end nucleoside unit introduced thereon-as represented by formula II:

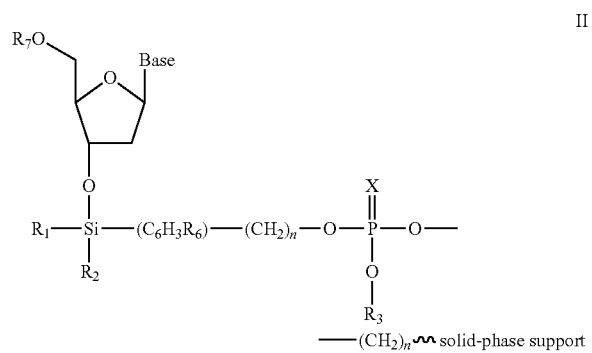

wherein

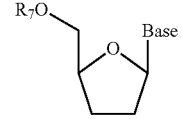

of formula II represents a 2'-deoxyribonucleoside or its N-protected derivative, the substituent $-O-(R_1)Si(R_2)-(C_6H_3R_6)-(CH_2)_n-O-P(OR_3)XO)-(CH^2)_n$ is attached at the 3' position of the sugar moiety of the nucleoside substituent; each of $R_1$ and $R_2$ is an alkyl or optionally substituted aryl group, wherein the optionally substituted aryl group has a substituent selected from the group consisting of $C_{1-4}$ alkyl, nitro, cyano, halo and methoxyl; $R_3$ is a protecting group; X is S or O; $R_7$ is H or 4,4'-dimethoxytrityl; each n is an integer of from 1 to 5; and the solid-phase support has hydroxyl groups on its surface.

13 Claims, 1 Drawing Sheet

3'-END NUCLEOSIDE UNIT COMPRISING PHOSPHORAMIDITE

This application is a National Stage Application under 35 U.S.C. §371(c) of PCT Application Ser. No. PCT/JP2005/002058, filed Feb. 10, 2005, which claims the priority of Japanese Patent Application No. 2004-049312 filed Feb. 25, 2004. The entire disclosure and contents of the above applications are hereby incorporated by reference herein.

FIELD OF THE INVENTION

The invention relates to a 3'-end nucleoside unit that is be advantageously used in a phosphoramidite method without protecting a base moiety, which was developed by the present inventors.

BACKGROUND ART

In conventional DNA synthesis methods, the introduction of a 3'-end nucleoside unit on a solid-phase support was done by the formation of amide bond with an amino group on the solid-phase support using a linker such as a succinate linker or silyl linkers for the 3'-end nucleoside.

For example, a benzoic acid-type compound: $iP_2Si—C_6H_4—C(O)$-type that was developed by one of the present inventors, SEKINE Mitsuo, is known as a silyl linker that can be cut out under a neutral condition (Non-Patent Document 1). However, since such silyl linker will be introduced into amino groups on the solid-phase support by acylation, the amino groups contained in dA, dC and dG have to be protected in advance with an appropriate protecting group such as DMTr.

Furthermore, as the DMTr protecting group in the base moiety of dC is relatively stable, treatment with 5% trifluoroacetic acid-$CH_2Cl_2$ solution for 30 min would be required to completely remove said protecting group. However, SiO bonds contained in the silyl linker and those formed between the silyl linker and a synthesized DNA oligomer would likely be cleaved under such a very acidic condition as in the above treatment.

Non-Patent Document 1: Wada, T.; Mochizuki, A.; Sato, T.; Seike, M.; M., Tetrahedron Letters, 1998, 39, 5593-5596

SUMMARY OF THE INVENTION

Problems to be Solved by the Invention

The purpose of the present invention is therefore to provide a method for binding a 3'-end nucleoside unit comprising any base to a hydroxyl group on a solid-phase support under completely the same condition as in DNA chain elongation reaction. Thus, as the DNA chain elongation reaction can be carried out with almost 100% reaction efficiency, the present inventors have studied hard in order to enable the introduction reaction of the 3'-end nucleoside unit on the solid-phase support under the same condition. Finally, the present inventors have solved the above problems by introducing a silyl linker and a phosphoramidite group into the 3'-end nucleoside unit and have completed the present invention.

The present invention relates to a 3'-end nucleoside unit comprising phosphoramidite that is a compound represented by the following formula:

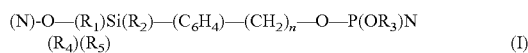

(I)

wherein (N) represents any nucleoside or its derivative, each of $R_1$, $R_2$ and $R_5$ is an alkyl or aryl group, $R_3$ is a phosphate-protecting group, and n is an integer of from 1 to 5.

The present invention further relates to a solid-phase support having said 3'-end nucleoside unit, for example, at a ratio of 20-30 μmol/g; to a method for the synthesis of a nucleic acid oligomer with the use of said solid-phase support, especially, to a phosphoramidite method with the use of an activating agent comprising an alcohol-type compound, or a mixture of the alcohol-type compound and an acid catalyst.

Advantages of the Invention

The solid-phase supports having hydroxyl groups on their surfaces area are now available by using the 3'-end nucleoside unit comprising the phosphoramidite according to the present invention. DNA synthesized with the use of the above phosphoramidite unit would be hardly cut out even under a basic condition such as with ammonia in contrast to the conventional methods. Furthermore, if the phosphoramidite unit comprising the silyl inker according to the present invention is used in the phosphoramidite method without the protecting base moiety, which was developed by the present inventors, no protecting group for the base moiety of the nucleic acids will be necessary in a process of the introduction of the nucleoside on the solid-phase support.

BRIEF DESCRIPTION OF DRAWING

FIG. 1B shows the retention time in minutes for the DNA oligomer d[TTTTTTTTTA] using the same HPLC conditions.

BEST MODE FOR CARRYING OUT THE INVENTION

Figure 1:
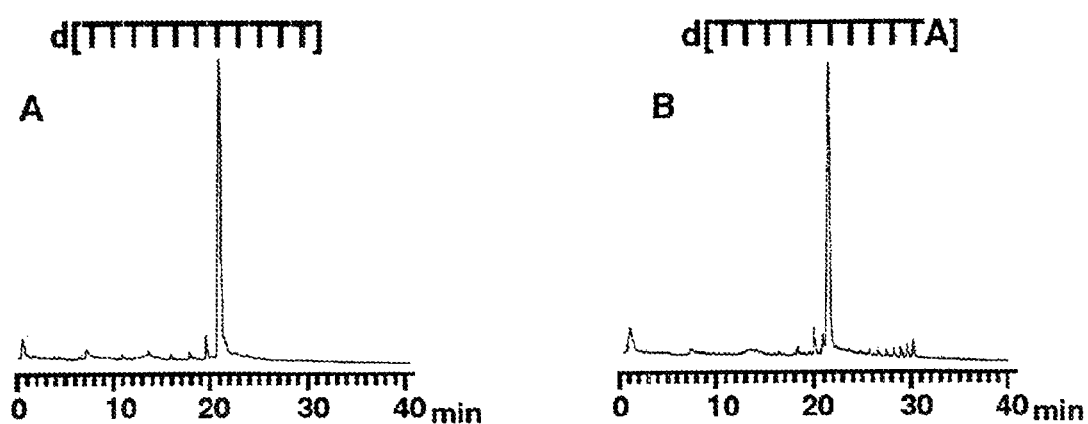
FIG. 1 shows HPLC charts showing detection of two different DNA oligomers prepared by methods of the present invention using an anion-exchange column. FIG. IA shows the retention time in minutes for the DNA oligomer d[TTTTTTTTTT]

The silyl group may have any substituents of R1 and R2 known for those skilled in the art, such as, for example, an alkyl group having 1 to 5 carbon atoms or an aryl group such as benzyl, phenyl and naphthyl group, which may have a substituent of the above alkyl, nitro, cyano, halogeno or alkoxy group at any position.

Any phosphate-protecting group known for those skilled in the art may be used, 2-cyanoethyl, 4-nitrophenyethyl, N-(trifluoroacetyl)aminobutyl, or 4-[N-methyl-N-(2,2,2-trifluoroacetyl)amino]butyl group being preferable.

R4 and R5 in the above formula are an alkyl having 1 to 4 carbon atoms, or aryl such as benzyl, phenyl and naphthyl group, an isopropyl group being preferable.

Furthermore, the benzene ring structure of the present compound may have any substituent known for those skilled in the art, which, for example, is selected from the group consisting of alkyl having 1 to 4 carbon atoms, halogeno, nitro, cyano and methoxy groups. The groups of "—CONH—" and "Si" are bound to the benzene ring in a para-position.

The compound of the present invention may be easily synthesized by those skilled in the art with reference to the following examples. Conditions that are not specifically described in the present specification may be optionally selected by those skilled in the art.

EXAMPLES

The present invention will be explained more in detail in line with the examples, which should not be construed to impose any limitations on the scope of the present invention.

4-diisopropylsilanylbenzoic acid methyl ester (2)

4-diisopropylsilanylbenzoic acid (9 g, 38 mmol) was dissolved in methanol (300 mL), and conc. $H_2SO_4$ (15 mL) was added dropwise to the solution cooled on ice. After being heated to reflux for 2 hours, the reaction solution was dissolved in chloroform (500 mL). The solution was then extracted two times with water (300 mL) and three times with 5 wt % aqueous solution (300 ml) of sodium hydrogen carbonate. An organic layer was collected and dehydrated with anhydrous sodium sulfate and filtered so that the resulting solvent was distilled out under a reduced pressure. The resulting crude product was then purified by silica gel column chromatography. After eluted with hexane having 0-5% ethyl acetate gradient, the solvent was distilled out to give a desired product (8.8 g, 93%). Its NMR data are as follows:

$^1$H NMR (CDCl$_3$): 0.93-1.06 (m, 12H), 1.18-1.27 (m, 2H), 3.90 (s, 3H), 3.96 (t, 1H, J=3.2 Hz), 7.58 (d, 2H, J=8.1 Hz), 7.98 (d, 2H, J=8.1 Hz).

$^{13}$C NMR (CDCl$_3$): 10.6, 18.5, 18.6, 52.2, 128.1, 128.2, 128.3, 130.5, 140.6, 167.1.

4-(hydroxymethyl)phenyl-diisopropylsilane (3)

LiAlH$_4$ (1.2 g, 32 mmol) was dissolved in anhydrous THF (80 mL), and to this was slowly added dropwise the anhydrous THF solution (80 mL) 4-diisopropylsilanylbenzoic acid methyl ester (2) (8 g, 32 mmol). The resulting mixture was then stirred for 10 min and ethyl acetate (20 mL) was added slowly to it. The reaction mixture was diluted with dichloromethane (500 mL), and then extracted three times with 0.2 N hydrochloric acid aqueous solution (400 mL). An organic layer was collected and dehydrated with anhydrous sodium sulfate and filtered so that the resulting solvent was distilled out under a reduced pressure to give a desired product (7.2 g, quant). Its NMR data are as follows:

$^1$H NMR (CDCl$_3$): 1.02 (2d, 12H, J=7.3 Hz), 1.17-1.23 (m, 2H), 3.09 (brs, 1H), 3.94 (t, 1H, J=3.2 Hz), 4.58 (s, 2H), 7.29 (d, 2H, J=7.6 Hz), 7.48 (d, 2H, J=7.6 Hz).

$^{13}$C NMR (CDCl$_3$): 10.7, 18.4, 18.6, 64.8, 126.0, 132.9, 135.4, 141.6.

4-(acetoxymethyl)phenyl-diisopropylsilane (4)

Acetic anhydride (3.1 mL, 33 mmol) and 4-N,N-dimethylaminoprydine (7.3 mg, 6 mmol) were added under argon atmosphere to pyridine (100 mL) dissolving 4-(hydroxymethyl)phenyl-diisopropylsilane (3) (4.9 g, 22 mmol). The resulting mixture was then stirred for 2 hours at a room temperature and methanol (20 mL) was added to it. The reaction mixture was diluted with ethyl acetate (400 mL), and then extracted three times with saturated saline solution (300 mL). An organic layer was collected and dehydrated with anhydrous sodium sulfate and filtered so that the resulting solvent was distilled out under a reduced pressure to give a desired product (5.4 g, 93%). Its NMR data are as follows:

$^1$H NMR (CDCl$_3$): 1.03 (2d, 12H, J=7.0 Hz), 1.20-1.24 (m, 2H), 2.09 (s, 3H), 3.96 (t, 1H, J=3.1 Hz), 5.10 (s, 2H), 7.32 (d, 2H, J=8.1 Hz), 7.51 (d, 2H, J=8.1 Hz).

$^{13}$C NMR (CDCl$_3$): 10.7, 18.4, 18.6, 20.9, 66.1, 127.1, 134.0, 135.5, 136.5, 170.4.

5'-[O-(4,4'-dimethoxytrityl)], 3'-[O-4-(acetoxymethyl)phenyl-diisopropylsilyl]thymidine (5t)

1,3-dichloro-4,4-dimethylhydantoin (761 mg, 3.9 mmol) was added to anhydrous CH$_2$Cl$_2$ solution (10 mL) of 4-(acetoxymethyl)phenyl-diisopropylsilane (4) (508 mg, 1.9 mmol). The resulting mixture was then stirred for 30 min at a room temperature and added to anhydrous CH$_2$Cl$_2$ solution (10 mL) dissolving 5'-O-(4,4'-dimethoxytrityl)thymidine (954 mg, 1.8 mmol) and imidazole (595 mg, 8.8 mmol). The reaction mixture was stirred for 30 min at a room temperature and mixed with water (5 mL). After 5 min, the reaction mixture was diluted with chloroform (100 ml) and extracted three times with 5 wt % aqueous solution (100 ml) of sodium hydrogen carbonate. An organic layer was collected and dehydrated with anhydrous sodium sulfate and filtered so that the resulting solvent was distilled out under a reduced pressure. The resulting crude product was then purified by silica gel column chromatography (1% pyridine). After eluted with hexane having 50-100% chloroform gradient and chloroform having 0-3% methanol gradient, the solvent was distilled out to give a desired product (1.1 g, 75%). Its NMR data are as follows:

$^1$H NMR (CDCl$_3$): 0.95-1.07 (m, 12H), 1.18-1.26 (m, 2H), 1.53 (s, 3H), 2.09 (s, 3H), 2.27-2.31 (m, 1H), 2.48-2.56 (m, 1H), 3.39 (d, 1H, J=8.1 Hz), 3.50 (d, 1H, J=8.6 Hz), 3.75 (s, 6H), 4.16 (d, 1H, J=2.4 Hz), 4.67 (d, 1H, J=5.7 Hz), 5.11 (s, 2H), 6.51 (t, 1H, J=4.1 Hz), 6.82 (dd, 4H, J=2.4 Hz, J=8.9 Hz), 7.18-7.67 (m, 14H), 10.3 (brs, 1H).

$^{13}$C NMR (CDCl$_3$): 11.7, 11.8, 11.9, 12.4, 16.8, 17.1, 17.16, 17.19, 17.21, 20.7, 41.6, 54.9, 63.1, 65.8, 73.1, 77.2, 84.7, 86.6, 86.8, 110.8, 112.9, 123.4, 124.9, 126.7, 126.9, 127.1, 127.6, 127.7, 127.8, 129.7, 133.3, 134.1, 134.4, 134.97, 135.01, 135.2, 135.7, 136.5, 143.9, 149.1, 150.3, 158.3, 163.9, 170.4.

MS m/z calcd for M+Na; 829.3496. Found; 829.3452.

5'-[O-(4,4'-dimethoxytrityl)], 3'-[O-4-(acetoxymethyl)phenyl-diisopropylsilyl],2-deoxyadenosine (5a)

4-(acetoxymethyl)phenyl-diisopropylsilane (4) (420 mg, 1.6 mmol) was dissolved in anhydrous CH$_2$Cl$_2$ solution (8 mL), and 1,3-dichloro-4,4-dimethylhydantoin (629 mg, 3.2 mmol) was added to it. The resulting mixture was then stirred for 30 min at a room temperature and added to anhydrous CH$_2$Cl$_2$ solution (8 mL) dissolving 5'-O-(4,4'-dimethoxytrityl)-2'-deoxyadenosine (796 mg, 1.4 mmol) and imidazole (489 mg, 7.2 mmol). The reaction mixture was stirred for 30 min at a room temperature and mixed with water (5 mL). After 5 min, the reaction mixture was diluted with chloroform (100 ml) and extracted three times with 5 wt % aqueous solution (100 ml) of sodium hydrogen carbonate. An organic layer was collected and dehydrated with anhydrous sodium sulfate and filtered so that the resulting solvent was distilled out under a reduced pressure. The resulting crude product was then purified by silica gel column chromatography (1% pyridine). After eluted with hexane having 50-100% chloroform gradient and chloroform having 0-3% methanol gradient, the solvent was distilled out to give a desired product (850 mg, 72%). Its NMR data are as follows:

$^1$H NMR (CDCl$_3$): 0.98-1.07 (m, 12H), 1.22-1.31 (m, 2H), 2.11 (s, 3H), 2.48-2.55 (m, 1H), 2.75-2.89 (m, 1H), 3.31 (d, 1H, J=4.6 Hz), 3.38 (d, 1H, J=4.6 Hz), 3.76 (s, 6H), 4.28 (d, 1H, J=2.4 Hz), 4.67 (t, 1H, J=2.6 Hz), 5.10 (s, 2H), 6.09 (s,

1H), 6.50 (dd, 1H, J=5.9 Hz, J=7.3 Hz), 6.76 (d, 4H, J=8.6 Hz), 7.17-7.38 (m, 11H), 7.50 (d, 2H, J=7.3 Hz), 7.99 (s, 1H), 8.28 (s, 1H).

$^{13}$C NMR (CDCl$_3$): 12.1, 12.2, 17.4, 21.0, 40.9, 55.2, 63.5, 66.1, 73.5, 84.5, 86.4, 87.1, 112.9, 113.0, 119.9, 126.7, 127.2, 127.7, 128.0, 129.9, 133.7, 134.6, 135.48, 135.51, 137.0, 138.8, 144.3, 149.4, 152.6, 155.3, 158.3, 170.6

MS m/z calcd for M+H, 816.3793. Found; 816.3711.

5'-[O-(4,4'-dimethoxytrityl)], 3'-[O-4-(hydroxymethyl)phenyl-diisopropylsilyl]thymidine (6t)

5'-[O-(4,4'-dimethoxytrityl)], 3'-[O-4-(acetoxymethyl)phenyl-diisopropylsilyl]thymidine (5t) (925 mg, 1.2 mmol) was treated with tBuNH$_2$-MeOH (1:4, v/v, 20 mL) for 3 hours at a room temperature. The reaction mixture was diluted with chloroform (100 mL), and then extracted three times with saturated saline solution (100 mL). An organic layer was collected and dehydrated with anhydrous sodium sulfate and filtered so that the resulting solvent was distilled out under a reduced pressure. The resulting crude product was then purified by silica gel column chromatography (1% pyridine). After eluted with hexane having 50-100% chloroform gradient and chloroform having 0-3% methanol gradient, the solvent was distilled out to give a desired product (781 mg, 89%). Its NMR data are as follows:

$^1$H NMR (CDCl$_3$): 0.92-1.00 (m, 12H), 1.17-1.25 (m, 2H), 1.56 (s, 3H), 2.15-2.38 (m, 1H), 2.53-2.68 (m, 1H), 3.31 (dd, 1H, J=2.7 Hz, J=10.5 Hz), 3.43 (dd, 1H, J=2.7 Hz, J=10.5 Hz), 3.77 (s, 6H), 4.12 (d, 1H, J=2.4 Hz), 4.63 (t, 1H, J=2.7 Hz), 4.67 (d, 1H, J=5.7 Hz), 6.44 (dd, 1H, J=5.9 Hz, J=7.3 Hz), 6.77 (dd, 4H, J=2.4 Hz, J=8.9 Hz), 7.19-7.35 (m, 11H), 7.44 (d, 2H, J=7.8 Hz), 7.61 (s, 1H), 8.15 (brs, 1H).

$^{13}$C NMR (CDCl$_3$): 12.0, 17.4, 41.8, 55.2, 63.3, 64.9, 73.3, 84.8, 86.8, 87.1, 111.0, 113.1, 126.1, 126.9, 127.8, 129.8, 129.9, 132.4, 134.5, 135.0, 135.2, 135.5, 142.2, 144.1, 150.3, 158.4, 163.9.

MS m/z calcd for M+H, 787.3391. Found; 787.3413.

5'-[O-(4,4'-dimethoxytrityl)], 3'-[O-4-(hydroxymethyl)phenyl-diisopropylsilyl],2-deoxyadenosine (6a)

5'-[O-(4,4'-dimethoxytrityl)], 3'-[O-4-(acetoxymethyl)phenyl-diisopropylsilyl]2-deoxyadenosine (5a) (610 mg, 0.75 mmol) was treated with tBuNH$_2$-MeOH (1:4, v/v, 15 mL) for 3 hours at a room temperature. The reaction mixture was diluted with chloroform (100 mL), and then extracted three times with saturated saline solution (100 mL). An organic layer was collected and dehydrated with anhydrous sodium sulfate and filtered so that the resulting solvent was distilled out under a reduced pressure. The resulting crude product was then purified by silica gel column chromatography (1% pyridine). After eluted with hexane having 50-100% chloroform gradient and chloroform having 0-3% methanol gradient, the solvent was distilled out to give a desired product (530 mg, 92%). Its NMR data are as follows:

$^1$H NMR (CDCl$_3$): 0.93-1.03 (m, 12H), 1.20-1.29 (m, 2H), 2.48-2.55 (m, 1H), 2.75-2.89 (m, 1H), 3.22 (dd, 1H, J=4.1 Hz, J=10.3 Hz), 3.39 (dd, 1H, J=4.1 Hz, J=10.3 Hz), 3.73 (s, 6H), 4.21 (d, 1H, J=3.8 Hz), 4.69 (s, 3H), 6.01 (s, 2H), 6.50 (t, 1H, J=6.2 Hz), 6.74 (d, 4H, J=8.9 Hz), 7.13-7.33 (m, 11H), 7.50 (d, 2H, J=8.1 Hz), 7.81 (s, 1H), 8.26 (s, 1H).

$^{13}$C NMR (CDCl$_3$): 12.2, 12.3, 17.46, 17.51, 17.55, 17.6, 40.8, 55.2, 63.2, 64.9, 73.0, 77.2, 84.2, 86.4, 86.7, 113.0, 119.8, 123.6, 126.3, 126.7, 127.7, 128.0, 128.1, 128.9, 129.87, 129.9, 132.6, 134.7, 135.5, 135.6, 135.8, 138.7, 142.5, 144.4, 149.6, 149.6, 152.8, 155.3, 158.3.

MS m/z calcd for M+H, 774.3687. Found; 774.3747.

5'-[O-(4,4'-dimethoxytrityl)], 3'-O—[O-4-(2-cyanoethyl N,N-diisopropylphosphoramidite) benzyl-diisopropylsilyl]thymidine (7t)

5'-[O-(4,4'-dimethoxytrityl)], 3'-O-[4-O-(hydroxymethyl)phenyl-diisopropylsilyl]thymidine (6t) (770 mg, 1.0 mmol) was subjected to azeotropic distillation sequentially with pyridine, toluene and dichloromethane to be dehydrated and dissolved in anhydrous THF (10 mL). To the resulting solution was added diisopropylethylamine (242 μL, 1.1 mmol) and (2-cyanoethyl) (N,N-diisopropylamino)chlorophosphine (242 μL, 1.5 mmol). After being stirred for 30 min, the reaction solution was poured into water (20 mL) and diluted with chloroform (200 mL), and then extracted three times with saturated saline solution (200 mL). An organic layer was collected and dehydrated with anhydrous sodium sulfate and filtered so that the resulting solvent was distilled out under a reduced pressure. The resulting crude product was then purified by silica gel column chromatography (1% triethylamine). After eluted with hexane having 50-100% chloroform gradient and chloroform having 0-3% methanol gradient, the solvent was distilled out to give desired white solid (850 mg, 88%). Its NMR data are as follows:

$^1$H NMR (CDCl$_3$): 0.94-1.06 (m, 12H), 1.17-1.29 (m, 15H), 1.50 (s, 3H), 2.13-2.30 (m, 1H), 2.35-2.48 (m, 1H), 2.60 (t, 2H, J=6.3 Hz), 3.27 (dd, 1H, J=2.7 Hz, J=10.5 Hz), 3.45 (dd, 1H, J=2.7 Hz, J=10.5 Hz), 3.61-3.87 (m, 10H), 4.14 (d, 1H, J=2.1 Hz), 4.65-4.76 (m, 3H), 6.48 (dd, 1H, J=5.7 Hz, J=7.8 Hz), 6.80 (dd, 4H, J=2.4 Hz, J=8.9 Hz), 7.21-7.37 (m, 11H), 7.46 (d, 2H, J=7.6 Hz), 7.63 (s, 1H), 9.45 (brs, 1H).

$^{13}$C NMR (CDCl$_3$): 11.8, 11.9, 12.0, 12.4, 16.9, 17.1, 17.27, 17.32, 17.4, 20.3, 20.4, 22.8, 22.90, 22.94, 24.47, 24.55, 24.57, 24.7, 41.7, 43.0, 43.2, 45.2, 45.3, 55.1, 58.3, 58.5, 63.3, 65.0, 65.3, 67.8, 73.2, 77.2, 84.8, 86.7, 87.0, 110.9, 113.01, 113.04, 117.4, 126.0, 126.1, 126.8, 127.7, 127.8, 129.76, 129.80, 132.3, 134.0, 134.3, 135.0, 135.2, 135.4, 140.2, 140.3, 144.0, 150.2, 158.4, 163.8.

$^{31}$P NMR (CDCl$_3$): 149.3

5'-[O-(4,4'-dimethoxytrityl)], 3'-O-[4-O-(2-cyanoethyl N,N-diisopropylphosphoramidite)benzyl-diisopropylsilyl]2'-deoxyadenosine (7a)

5'-[O-(4,4'-dimethoxytrityl)], 3'-[O-4-(hydroxymethyl)phenyl-diisopropylsilyl]2'-deoxyadenosine (6a) (450 mg, 0.58 mmol) was subjected to azeotropic distillation sequentially with pyridine, toluene and dichloromethane to be dehydrated and dissolved in anhydrous THF (6 mL). To the resulting solution was added diisopropylethylamine (144 μL, 0.64 mmol). The resulting solution was cooled to −78° C., mixed with (2-cyanoethyl) (N,N-diisopropylamino)chlorophosphine (141 μL, 0.87 mmol) and then gradually brought back to a room temperature. After being stirred for 30 min, the reaction solution was poured into water (20 mL) and diluted with chloroform (200 mL), and then extracted three times with saturated saline solution (200 mL). An organic layer was collected and dehydrated with anhydrous sodium sulfate and filtered so that the resulting solvent was distilled out under a reduced pressure. The resulting crude product was then purified by silica gel column chromatography (1% triethylamine). After eluted with hexane having 50-100% chloroform gradient and chloroform having 0-3% methanol gradient, the solvent was distilled out to give desired white solid (500 mg, 87%). Its NMR data are as follows:

$^1$H NMR (CDCl$_3$): 0.98-1.05 (m, 12H), 1.16-1.29 (m, 15H), 2.48-2.69 (m, 3H), 2.72-2.87 (m, 1H), 3.31 (dd, 1H, J=4.1 Hz, J=10.3 Hz), 3.39 (dd, 1H, J=4.1 Hz, J=10.3 Hz), 3.60-3.86 (m, 10H), 4.28 (d, 1H, J=2.4 Hz), 4.67-4.78 (m,

3H), 6.06 (s, 2H), 6.51 (t, 1H, J=6.4 Hz), 6.77 (d, 4H, J=8.6 Hz), 7.18-7.38 (m, 11H), 7.49 (d, 2H, J=7.0 Hz), 7.98 (s, 1H), 8.28 (s, 1H).

$^{13}$C NMR (CDCl$_3$): 12.2, 12.3, 17.46, 17.51, 17.55, 17.6, 40.8, 55.2, 63.2, 64.9, 73.0, 77.2, 84.2, 86.4, 86.7, 113.0, 119.8, 123.6, 126.3, 126.7, 127.7, 128.0, 128.1, 128.9, 129.87, 129.9, 132.6, 134.7, 135.5, 135.6, 135.8, 138.7, 142.5, 144.4, 149.5, 149.6, 152.8, 155.3, 158.3.

$^{31}$P NMR (CDCl$_3$): 149.3.

Triethylammonium, O-(4,4'-dimethoxytrityl)acetic acid (9)

4,4'-dimethoxytrityl chloride was added to pyridine solution (100 mL) dissolving hydroxyacetic acid (760 mg, 10 mmol) and triethylamine (1.45 mL, 11 mmol). Stirring for 24 hours at a room temperature gave 20 mL of ethanol, which was diluted with chloroform (500 mL) and extracted three times with 0.5 M triethylammonium carbonate buffer (300

[Chemical formula 1]

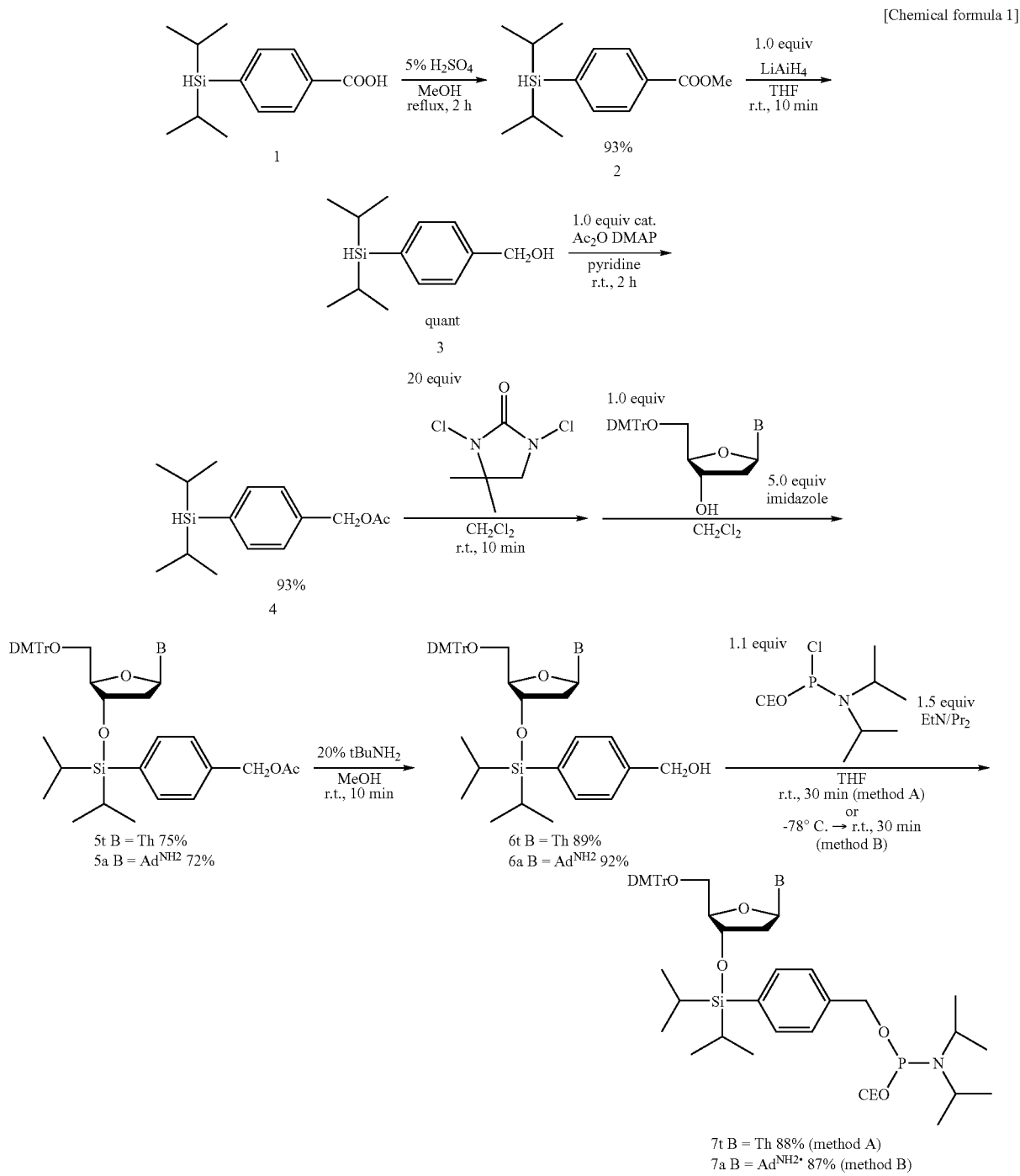

mL). An organic layer was collected and dehydrated with anhydrous sodium sulfate and filtered so that the resulting solvent was distilled out under a reduced pressure. The resulting crude product was then purified by silica gel column chromatography. After eluted with chloroform having 0-3% methanol gradient, the solvent was distilled out to give a desired product (3.5 g, 73%). Its NMR data are as follows:

$^1$H NMR (CDCl$_3$): 1.15 (t, 9H, J=7.3 Hz), 2.97 (dd, 6H, J=7.0 Hz, J=14.9 Hz), 3.55 (s, 2H), 3.64 (s, 6H), 6.77 (dd, 4H, J=2.4 Hz, J=7.0 Hz), 7.06-7.17 (m, 3H), 7.39 (dd, 4H, J=2.0 Hz, J=7.4 Hz), 7.43 (d, 2H, J=1.4 Hz).

Preparation of a Solid-Phase Support (10)

Solid-phase support (highly cross-linked polystyrene: HCP) sufficiently dried (500 mg, 17 μmol), triethylammonium, O-(4,4'-dimethoxytrityl)acetic acid 3-18 (260 μmol) and DCC (268 mg 1.3 mmol) were dissolved into dichloromethane (5 mL) and stirred for 12 hours at a room temperature. After the completion of the reaction, the solid-phase support was filtered, washed with acetonitrile, dried and added to pyridine solution (4.5 mL) of acetic anhydride (0.5 ml) and DMAP (5 mg). After being stirred for 3 hours, the solid-phase support was filtered again and washed with acetonitrile. The introduction ratio of the compound was measured by colorimetric determination of the trityl group (24 μmol/g).

[Chemical formula 2]

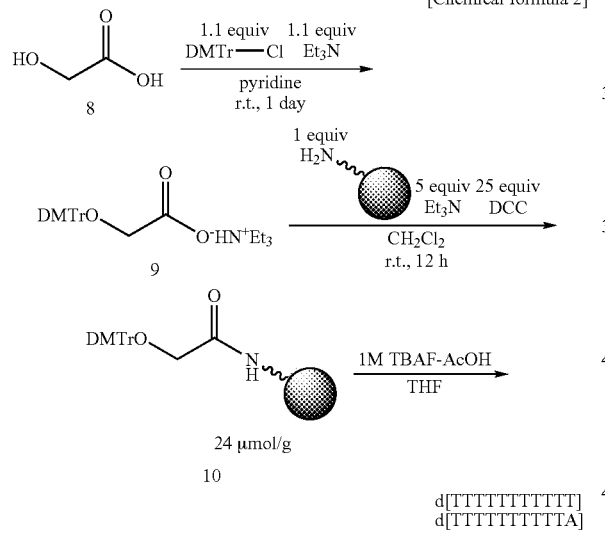

DNA Synthesis with the Use of the Silyl Linker

The synthesis of d[TTTTTTTTTT] and d[TTTTTTTTTA] was carried out with the use of the HCP solid-phase support (1 μmol, 24 μmol/g) and the phosphoramidite unit (7t) or (7a) comprising the silyl linker, or thymidine 3' phosphoramidite unit by means of DNA/RNA Synthesizer 392 (Applied Biosystem Inc.: ABI). Each elongation cycle of the oligomer was shown in TABLE 1 below.

TABLE 1

| step | operation | Reagent(s) | time, (min) |
|---|---|---|---|
| 1 | washing | CH$_3$CN | 0.2 |
| 2 | detritylation | 3% Cl$_3$CCOOH/CH$_2$Cl$_2$ | 1.5 |
| 3 | washing | CH$_3$CN | 0.4 |
| 4 | coupling | 0.1M amidite + 0.2M HO$^d$Bt in CH$_3$CN—NMP (15:1, v/v) | 1.0 |
| 5 | washing | CH$_3$CN | 0.2 |
| 6 | coupling | 0.1M amidite + 0.2M HO$^d$Bt in CH$_3$CN—NMP (15:1, v/v) | 1.0 |

TABLE 1-continued

| step | operation | Reagent(s) | time, (min) |
|---|---|---|---|
| 7 | washing | CH$_3$CN | 0.2 |
| 8 | oxidation | 0.1M I$_2$ in Py-H$_2$O-THF (20:2:78, v/v/v) | 0.5 |
| 9 | washing | CH$_3$CN | 0.4 |

The DMTr group was then removed by the treatment with 3% trichloroacetic acid in CH$_2$Cl$_2$ (2 mL) for one minute, and the solid-phase support was washed with CH$_2$Cl$_2$ (1 mL×3) and CH$_3$CN (1 mL×3). The cyanoethyl group was then removed by the treatment with 10% DBU in CH$_3$CN (500 μL). After being washed with CH$_3$CN (1 mL×3), the solid-phase support was treated with anhydrous THF solution (500 μL) dissolving TBAF (131 mg, 0.5 mmol) and acetic acid (24 μL, 0.5 mmol) for one hour in order to cut out the DNA oligomer. The resulting mixture solution was desalted with Sep-Pak C18 cartridge to give a desired product.

INDUSTRIAL APPLICABILITY

Various solid-phase material may be selected by using the 3'-end nucleoside unit comprising phosphoramidite according to the present invention, making it possible to synthesize a high through-put DNA chip wherein the solid-phase may be directly used as the chip.

What is claimed is:

1. A compound represented by the following formula:

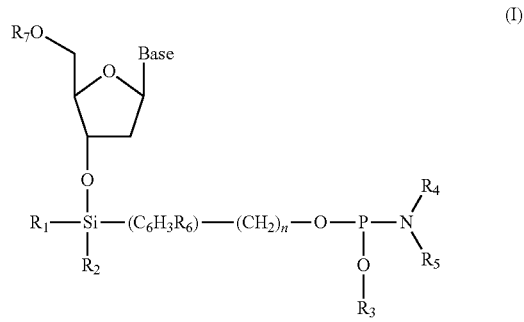

(I)

wherein

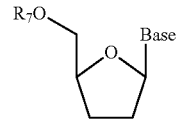

of formula I represents a 2'-deoxyribonucleoside or its N-protected derivative, the substituent —O—(R$_1$)Si (R$_2$)—(C$_6$H$_3$R$_6$)—(CH$_2$)$_n$—O—P(OR$_3$)N(R$_4$)(R$_5$) is attached at the 3' position of the sugar moiety of the nucleoside substituent; each of R$_1$, R$_2$, R$_4$ and R$_5$ is an alkyl or optionally substituted aryl group, wherein the optionally substituted aryl group has a substituent selected from the group consisting of C$_{1-5}$ alkyl, nitro, cyano, halo and methoxyl; R$_3$ is a protecting group; R$_6$ substituent of the benzene ring —(C$_6$H$_3$R$_6$)— is selected from the group consisting of H, C$_{1-4}$ alkyl, halo, nitro, cyano and methoxyl; R$_7$ is H or 4,4'-dimethoxytrityl; and n is an integer of from 1 to 5.

2. The compound according to claim 1 wherein R$_1$ and R$_2$ are independently a C$_{1-5}$ alkyl.

3. The compound according to claim 1 wherein R$_1$ and R$_2$ are independently substituted aryl.

4. The compound according to any one of claims 1 to 3 wherein the protecting group R$_3$ is 2-cyanoethyl, 4-nitrophenylethyl, N-(trifluoroacetyl)aminobutyl, or 4-[N-methyl-N-(2,2,2-trifluoroacetyl)amino]butyl.

5. The compound according to claim 4 wherein the protecting group $R_3$ is 2-cyanoethyl.

6. The compound according to claim 1 wherein each of $R_4$ and $R_5$ is independently $C_{1-4}$ alkyl, benzyl, phenyl, or naphthyl.

7. The compound according to claim 1 wherein each of $R_4$ and $R_5$ is independently isopropyl.

8. The compound according to claim 1 wherein $R_6$ is selected from the group consisting of $C_{1-4}$ alkyl, halo, nitro, cyano and methoxy.

9. A compound having the structure

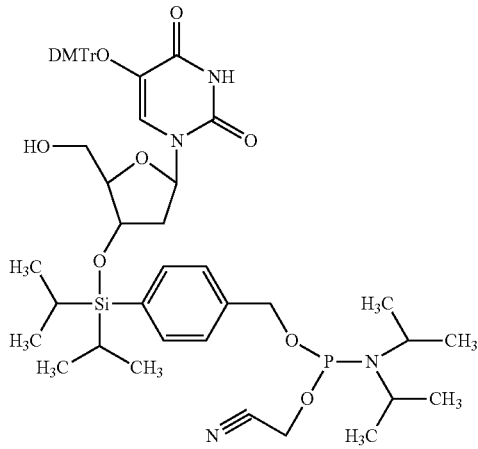

wherein DMTr is 4,4'-dimethoxytrityl.

10. A compound having the structure

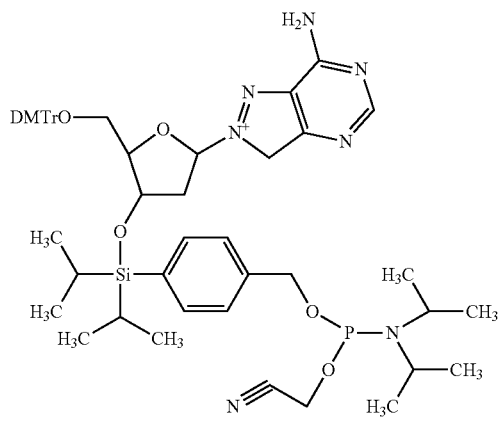

wherein DMTr is 4,4'-dimethoxytrityl.

11. A solid-phase support having a 3'-end nucleoside unit introduced thereon as represented by formula II:

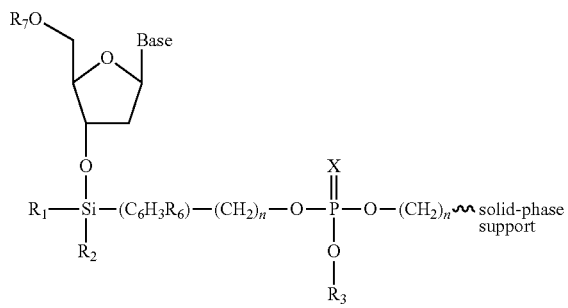

wherein

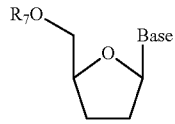

of formula II represents a 2'-deoxyribonucleoside or its N-protected derivative, the substituent —O—($R_1$)Si($R_2$)—($C_6H_3R_6$)—$(CH_2)_n$—O—P($OR_3$)XO)—$(CH_2)_n$ is attached at the 3' position of the sugar moiety of the nucleoside substituent; each of $R_1$ and $R_2$ is an alkyl or optionally substituted aryl group, wherein the optionally substituted aryl group has a substituent selected from the group consisting of $C_{1-4}$ alkyl, nitro, cyano, halo and methoxyl; $R_3$ is a protecting group; X is S or O; $R_7$ is H or 4,4'-dimethoxytrityl; each n is an integer of from 1 to 5; and the solid-phase support has hydroxyl groups on its surface.

12. The solid-phase support according to claim 11 having the 3'-end nucleoside units present at a ratio of 20-30 μmol/g.

13. The solid-phase support of claim 11, wherein the solid-phase support is a highly cross-linked polystyrene (HCP).

* * * * *